United States Patent
Aleo et al.

(10) Patent No.: US 12,390,429 B2
(45) Date of Patent: Aug. 19, 2025

(54) CHEMICALLY AND PHYSICALLY STABLE TOPICAL OPHTHALMIC NEPAFENAC-BASED FORMULATIONS

(71) Applicant: MEDIVIS S.R.L., Tremestieri Etneo (IT)

(72) Inventors: Danilo Aleo, Tremestieri Etneo (IT); Maria Grazia Saita, Tremestieri Etneo (IT); Barbara Melilli, Tremestieri Etneo (IT); Sergio Mangiafico, Tremestieri Etneo (IT); Melina Cro, Tremestieri Etneo (IT)

(73) Assignee: MEDIVIS S.R.L., Tremestieri Etneo (IT)

( * ) Notice: Subject to any disclaimer, the term of this patent is extended or adjusted under 35 U.S.C. 154(b) by 843 days.

(21) Appl. No.: 17/422,535

(22) PCT Filed: Jan. 14, 2020

(86) PCT No.: PCT/IB2020/050260
§ 371 (c)(1),
(2) Date: Jul. 13, 2021

(87) PCT Pub. No.: WO2020/148645
PCT Pub. Date: Jul. 23, 2020

(65) Prior Publication Data
US 2022/0096404 A1     Mar. 31, 2022

(30) Foreign Application Priority Data
Jan. 14, 2019   (IT) .................. 102019000000561

(51) Int. Cl.
*A61K 31/165*   (2006.01)
*A61K 9/00*   (2006.01)
*A61K 9/08*   (2006.01)
*A61K 31/202*   (2006.01)
*A61K 31/573*   (2006.01)
*A61K 47/40*   (2006.01)

(52) U.S. Cl.
CPC .......... *A61K 31/165* (2013.01); *A61K 9/0048* (2013.01); *A61K 9/08* (2013.01); *A61K 31/202* (2013.01); *A61K 31/573* (2013.01); *A61K 47/40* (2013.01)

(58) Field of Classification Search
CPC .. A61K 31/165; A61K 31/202; A61K 31/573; A61K 47/40; A61P 27/02
See application file for complete search history.

(56) References Cited

U.S. PATENT DOCUMENTS

| | | | |
|---|---|---|---|
| 2007/0203173 A1* | 8/2007 | Mudumba | A61K 33/00 514/291 |
| 2009/0092574 A1* | 4/2009 | Scott | A61P 27/16 424/78.04 |
| 2018/0055943 A1* | 3/2018 | Salzman | A61K 31/4725 |
| 2018/0147297 A1* | 5/2018 | Loftsson | A61K 9/0048 |

FOREIGN PATENT DOCUMENTS

| | | | | |
|---|---|---|---|---|
| EP | 2921171 A1 | 9/2015 | | |
| WO | WO-2008108927 A2 * | 9/2008 | ......... | A61K 38/2292 |

OTHER PUBLICATIONS

Watson et al. Common eye infections. Aust Prescr. 2018;41(3):67-72. (Year: 2018).*
International Search Report for International Patent Application No. PCT/IB2020/050260, mailed May 15, 2020, 11 Pages.

* cited by examiner

*Primary Examiner* — Joseph K McKane
*Assistant Examiner* — Ashli Ariana Chicks
(74) *Attorney, Agent, or Firm* — Armstrong Teasdale LLP

(57) ABSTRACT

Topical ophthalmic Nepafenac-based formulations, which are particularly stable from both chemical and physical points of view, are provided.

8 Claims, No Drawings

CHEMICALLY AND PHYSICALLY STABLE TOPICAL OPHTHALMIC NEPAFENAC-BASED FORMULATIONS

CROSS-REFERENCE TO RELATED APPLICATIONS

This application is a National Phase Application of PCT International Patent Application No. PCT/IB2020/050260, having an International Filing Date of Jan. 14, 2020, which claims priority to Italian Patent Application No. 102019000000561 filed Jan. 14, 2019, each of which is hereby incorporated by reference in its entirety.

FIELD OF THE INVENTION

The present invention finds application in the medical field and, in particular, it relates to particularly stable topical ophthalmic Nepafenac (NPF)-based formulations.

BACKGROUND OF THE INVENTION

In ophthalmology, the topical use of Nepafenac (NPF) is preferred over many other non-steroidal anti-inflammatory drugs due to its excellent pharmacokinetic profile, even at the retinal level.

For this reason, NPF is widely used for the treatment of post-surgical inflammatory and painful states and is approved for the prevention of cystoid macular edema, as well as for certain neurodegenerative diseases affecting the retina.

From a chemical point of view, however, Nepafenac is characterized by very low water solubility (0.014 mg/ml), which renders difficult its formulation in aqueous solution.

To date, in fact, the only commercially available medicinal preparations for ophthalmic use are represented by NPF suspensions at a concentration of 0.1% and 0.3%.

It is known that suspensions are characterized by poor patient compliance, due to the feeling of a foreign body and to irritation caused by the particles, inducing excessive tearing with the drug being subsequently washed away, thus preventing it from reaching high concentrations in the eye tissues.

This is also true of Nepafenac.

Considerable formulation efforts have been devoted to its suspensions with the aim of improving its pharmacokinetic profile.

Several authors have assessed the use of poloxamers, penetration enhancers, viscosizing or gelling polymers, and even nanoparticle systems (NLCs) in thermosensitive hydrogels with the aim of increasing the precorneal residence times of the drug and improving its transcorneal permeability.

In 2013, Alcon introduced a new 0.3% NPF suspension (ILEVRO 0.3% or NEVANAC 0.3%) for which better ocular bioavailability is shown thanks to certain technological expedients; in fact, the new suspension provides both the use of HP-Guar, in addition to carbomer (polymers known to increase precorneal residence time), and the reduction in the particle size of NPF to about a third of that of the 0.1% suspension.

Although this type of drug release system is technologically advanced, it still involves very viscous suspensions, which have the limits listed above.

By contrast, to date, formulation studies for obtaining stable aqueous NPF solutions have been poor.

The only ones concern the formation of complexes with β-cyclodextrins (β-CD), in particular with hydroxypropylβ-CD (Hpβ-CD) a,b,c and sulfobutyl etherβ-CD (SBEβ-CD) a,b wherein the maximum NPF concentration investigated is 0.1%.

Such studies have been carried out to investigate both the stoichiometry of the NPF/β-CD complex and the possible pharmacokinetic improvement, in terms of transcorneal permeability and precorneal residence time, with respect to the commercial suspension.

The results have shown that NPF in solution has a transcorneal permeation rate which is 18 times greater than Nevanac 0.1% and residence times which are 11 times greater.

Nonetheless, none of those works is capable of describing a formulation which is stable enough over time to be able to create a medicinal preparation thereof.

SUMMARY OF THE INVENTION

The inventors of the present patent application have surprisingly found that it is possible to make ophthalmic Nepafenac-based formulations that are stable from both a chemical and a physical point of view; such formulations may be stored for at least 24 months at room temperature maintaining a Nepafenac titer above 90% at all times.

In a first object, the present patent application describes topical pharmaceutical Nepafenac-based formulations for ophthalmic use comprising methyl-β-cyclodextrin.

In one aspect of the invention, such formulations comprise suitable hydrophilic polymers.

In another aspect, the formulations of the invention comprise further active ingredients.

In a further aspect, the formulations described have a pH comprised between 7.1 and 7.9, and preferably comprised between 7.5-7.8.

In a second object of the invention, there is described the use of methyl-β-cyclodextrin for the stabilization of ophthalmic pharmaceutical formulations for topical use comprising Nepafenac.

In a third object, there is described a process for the preparation of the formulations of the invention.

In a fourth object, the formulations of the invention are described for medical use.

In particular, the medical use is described for the treatment of post-surgical inflammatory and painful states, for the prevention of cystoid macular edema, for the treatment of retinal neurodegenerative diseases.

In a fifth object, there is described a method for the ophthalmic treatment of post-surgical inflammatory and/or painful states, for the prevention of cystoid macular edema, for the treatment of retinal neurodegenerative diseases comprising the administration of a formulation of the invention to a patient in need thereof.

DETAILED DESCRIPTION OF THE INVENTION

According to a first object, the present invention describes ophthalmic pharmaceutical Nepafenac-based formulations for topical use, which are stabilized from a chemical and a physical point of view.

In particular, the formulations of the invention comprise Nepafenac in an amount comprised between about 0.1%-0.5%, and preferably comprised between about 0.1%-0.3% (weight/total weight of the formulation).

Stabilization from a chemical point of view means that the active ingredient Nepafenac shows to be not degraded and to maintain a high titer even after a long time in the formulations of the invention.

Such stabilization effect may also show in relation to any further active ingredients comprised in the formulations.

For the purposes of the present invention, in the described formulations, the Nepafenac titer is ≥97% at 6 months, preferably ≥96% at 9 months, more preferably ≥95% at 12 months, even more preferably ≥93% at 18 months, and much more preferably ≥92% at 24 months.

Stabilization from a physical point of view means that no phenomena of precipitation, coalescence, flocculation, phase separation are observed in the formulations of the invention.

Preferably, such phenomena are not observed for 6 months, preferably for 9 months, more preferably for 12 months, even more preferably for 18 months and much more preferably for 24 months.

According to the present invention, the formulations described are stable because they comprise methyl-β-cyclodextrin (hereinafter abbreviated as Metβ-CD).

In one aspect of the invention, Metβ-CD is present in an amount comprised between about 1-5% and preferably comprised between about 3-5% (weight-total weight of the formulation).

According to one aspect of the invention, the formulations of the invention may comprise one or more hydrophilic polymers.

Preferably, such polymers are selected from polyvinyl pyrrolidone (PVP) and polyvinyl alcohol (PVA); therefore, polyvinyl pyrrolidone and/or polyvinyl acetate may be present in the formulations.

Such polymers are each present in the formulations in an amount comprised between about 0.5-1.5% (weight/total weight of the formulation).

For the purposes of the present invention, the preferred polyvinyl pyrrolidone is PVP 30, although other types of PVP are equally possible, such as, for example, PVP 15, 60, 90, 120, etc.

For the purposes of the present invention, the preferred polyvinyl acetate is PVA 28-99, although other types of PVA are equally possible, such as, for example, PVA 4-88, 8-88, 28-99, etc.

The use of PVP and PVA does not exclude the use of other hydrophilic polymers, or associations therebetween, which are compatible with an ophthalmic application.

According to an alternative aspect of the invention, hyaluronic acid may be used in addition to the hydrophilic polymers described above, preferably in an amount of about 0.05-0.15%, and more preferably about 0.10-0.15% (weight/total weight of the formulation), in order to make the preparation more mucoadhesive and impart rheological characteristics that improve its acceptability by the patient.

For the purposes of the present invention, the formulations have a pH comprised between about 7.1 and 7.9, and preferably comprised between about 7.5-7.8.

The formulations of the invention may comprise preservatives with a bacteriostatic action, for example selected from the group comprising: benzalkonium chloride, cetrimide or polyhexanide (PHMB) and sodium metabisulfite.

According to another aspect of the present invention, the formulations described may also contemplate the presence of other pharmacologically active molecules (active ingredients).

These may be selected from the group comprising: polyunsaturated fatty acids EPA and DHA (both in the Ethyl Ester EE and Acid AA form), cortisones selected from dexamethasone (DEX); betamethasone and hydrocortisone (HYD), both in the phosphate (DEX-P, HYD-P) and free alcohol (DEX-OH, HYD-OH) form; other cortisones for ophthalmic use.

As regards the other components of the formulations of the invention, these may comprise:

a buffer system, comprising buffering agents, selected from the group comprising: a sodium phosphate buffer system, which may be substituted with sodium and/or potassium citrate or with other buffers compatible with an ophthalmic use;

osmotizing agents selected from the group comprising: glycerol, mannitol, trehalose, sorbitol, in concentrations suitable to give solutions with an osmolality comprised between about 240 and 350 mOsm/kg. The latter two, in particular, do not cause variations in stability of the formulations.

In one aspect of the invention, the formulations described comprise Nepafenac in an amount of about 0.1-0.5%, Metβ-CD in an amount of about 3-5%, hydrophilic polymers in an amount of about 0.5-1% and have a pH of about 7.5-7.8.

Particular examples of such prepared formulations are illustrated in the following Table 1 (composition in % w/total weight of the formulation):

TABLE 1

| Component | Formulation | | | | | | | |
|---|---|---|---|---|---|---|---|---|
| | 1 | 2 | 3 | 4 | 5 | 6 | 7 | 8 |
| NPF | 0.1 | 0.1 | 0.3 | 0.5 | 0.1 | 0.10 | 0.4 | 0.3 |
| Metβ-CD | 3.0 | 4.0 | 4.0 | 5.0 | 3.5 | 3.0 | 5.0 | 4.0 |
| $Na_2HPO_4$ | 0.1 | 0.10 | 0.12 | 0.18 | 0.18 | 0.13 | 0.16 | 0.19 |
| $H_3PO_4$ (0.85%) | 0.5 | 0.5 | 0.4 | 0.5 | 0.5 | 0.4 | 0.3 | 0.4 |
| Glycerol | 0.9 | 0.9 | 0.9 | 0.8 | 0.9 | 0.9 | 0.8 | 0.7 |
| Mannitol | 1.0 | 1.0 | 1.0 | 1.0 | 1.0 | 1.0 | 1.0 | 1.0 |
| PVP | 1.0 | — | 1.5 | 1.0 | 1.0 | — | 1.5 | 1.5 |
| PVA | — | 1.0 | — | 1.5 | — | 0.5 | — | — |
| Hyaluronic Ac | 0.1 | 0.15 | 0.10 | 0.10 | 0.10 | 0.10 | 0.1 | 0.1 |
| EDTA-$Na_2*2H_2O$ | 0.02 | 0.02 | 0.03 | 0.02 | 0.02 | 0.02 | 0.03 | 0.02 |
| NaCl | — | 0.1 | 0.1 | — | 0.1 | 0.1 | — | — |
| pH | 7.5 | 7.5 | 7.6 | 7.8 | 7.8 | 7.7 | 7.8 | 7.8 |
| Purified water | q.s. 100 | q.s. 100 | q.s. 100 | q.s. 100 | q.s. 100 | q.s. 100 | q.s. 100 | q.s. 100 |

In a preferred aspect of the invention, the formulations described comprise Nepafenac in an amount of about 0.1-0.3%, Metβ-CD in an amount of about 3.5-4%, hydrophilic polymers in an amount of about 0.5-1% and have a pH of about 7.5-7.8.

Particular examples of such prepared formulations are illustrated in the following Tables 2A and 2B (composition in % w/total weight of the formulation):

TABLE 2A

| Component | Formulation | | | |
|---|---|---|---|---|
| | 9 | 10 | 11 | 12 |
| Nepafenac | 0.1 | 0.3 | 0.1 | 0.1 |
| Metβ-CD | 3.5 | 5.0 | 4.0 | 4.0 |
| $Na_2HPO_4$ | 0.12 | 0.14 | 0.18 | 0.18 |
| $H_3PO_4$ (0.85%) | 0.4 | 0.5 | 0.5 | 0.5 |

TABLE 2A-continued

| Component | Formulation 9 | 10 | 11 | 12 |
|---|---|---|---|---|
| Glycerol | 0.9 | 0.9 | 0.9 | 0.9 |
| Mannitol | 1.0 | 1.0 | 1.0 | 1.0 |
| API % | 0.1 DEX-P | 0.3 HYD-P | 0.1 DEX-OH | 0.01 DHA-EE |
| PVP-30 | 0.5 | | | |
| PVA | | 1.0 | 1.0 | 1.0 |
| Hyaluronic Ac. | 0.05 | 0.10 | 0.10 | 0.10 |
| EDTA-Na$_2$*2H$_2$O | 0.02 | 0.02 | 0.02 | 0.02 |
| NaCl | 0.1 | 0.1 | 0.1 | 0.1 |
| pH | 7.6 | 7.6 | 7.8 | 7.8 |
| Purified water | q.s. 100 | q.s. 100 | q.s. 100 | q.s. 100 |

TABLE 2B

| Component | Formulation 13 | 14 | 15 |
|---|---|---|---|
| Nepafenac | 0.1 | 0.1 | 0.1 |
| Metβ-CD | 4.0 | 4.0 | 3.5 |
| Na$_2$HPO$_4$ | 0.14 | 0.12 | 0.14 |
| H$_3$PO$_4$ (0.85%) | 0.5 | 0.5 | 0.5 |
| Glycerol | 0.9 | 0.9 | 0.9 |
| Mannitol | 1.0 | 1.0 | 1.0 |
| API % | 0.03 DHA-AA | 0.01 DHA-EE | 0.1 DEX-P |
| PVP-30 | 0.5 | | |
| PVA | | 0.5 | 0.5 |
| Hyaluronic Ac. | 0.15 | 0.10 | 0.15 |
| EDTA-Na$_2$*2H$_2$O | 0.02 | 0.02 | 0.02 |
| NaCl | 0.1 | 0.1 | 0.1 |
| pH | 7.6 | 7.5 | 7.6 |
| Purified water | q.s. 100 | q.s. 100 | q.s. 100 |

According to a second object of the invention, there is described the use of methyl-β-cyclodextrin for the chemical and physical stabilization of ophthalmic pharmaceutical formulations for topical use comprising Nepafenac.

In particular, such formulations are the formulations described in the present patent application.

According to a third object, there is described a process for the preparation of ophthalmic pharmaceutical formulations for topical use comprising Nepafenac.

In particular, the process comprises the step of solubilizing the active ingredient Nepafenac in a solution comprising Metβ-CD and the optional selected hydrophilic polymer, where such solution has a pH comprised between 7.1 and 7.9 and preferably comprised between 7.5-7.8.

In one aspect of the invention, such solubilization step may be carried out at a temperature comprised between 20° C. and 120° C.

In another aspect of the invention, such step may be carried out in a time comprised between 10 and 30 minutes.

Upon completing the solubilization step, the osmotizing agents, any other hydrophilic polymers are added and finally the last step of adjusting the pH to the desired value is carried out.

In a fourth object, the formulations of the invention according to the foregoing are described for medical use.

In particular, the medical use is described for the treatment of post-surgical inflammatory and/or painful states, for the prevention of cystoid macular edema, for the treatment of retinal neurodegenerative diseases.

In a fifth object, the present invention describes a method for the ophthalmic treatment of post-surgical inflammatory and/or painful states, for the prevention of cystoid macular edema, for the treatment of retinal neurodegenerative diseases comprising the administration of a formulation as described in the present patent application to a patient in need thereof.

The present invention will be better illustrated by the following examples, which are not to be construed as limiting.

Examples 1-6

Stability

Below is a comparative study between ophthalmic formulations containing Metβ-CD and formulations containing other β-cyclodextrins. Unlike the formulations containing Metβ-CD, those containing other cyclodextrins show a rate of degradation of the active ingredient which, after a few months, leads to a content of NPF significantly lower than 90% of its initial titer or even undergo formation of precipitates (see Table 3).

| Composition % w/w | Example 1 | Example 2 | Example 3 | Example 4 | Example 5 | Example 6 |
|---|---|---|---|---|---|---|
| Nepafenac | 0.1 | | 0.1 | 0.1 | 0.1 | 0.1 |
| Metβ-CD | 3.0 | 4.0 | | | | |
| Hpβ-CD | | | 4.0 | 6.0 | 4.0 | |
| SBEβ-CD | | | | | | 6.0 |
| Na$_2$HPO$_4$ | 0.1 | 0.1 | 0.1 | 0.1 | 0.1 | 0.1 |
| H$_3$PO$_4$ (0.85%) | 0.5 | 0.5 | 0.5 | 0.5 | 0.5 | 0.5 |
| Glycerol | 0.9 | 0.9 | 0.9 | 0.9 | 0.9 | |
| Mannitol | 1.0 | 1.0 | 1.0 | 1.0 | 1.0 | 0.8 |
| Hyaluronic Ac | | 0.10 | 0.15 | 0.10 | 0.10 | 0.10 |
| EDTA-Na$_2$*2H$_2$O | | 0.02 | 0.02 | 0.02 | 0.02 | 0.02 |
| NaCl | 0.1 | 0.1 | | 0.1 | 0.1 | |
| Purified water | q.s. 100 | q.s. 100 | q.s. 100 | q.s. 100 | q.s. 100 | q.s. 100 |

The following Table 4 shows the stability data on the formulations of examples 1 to 6.

| Months 25° C. | Ex. 1 (Metβ-CD) | Ex. 2 (Metβ-CD) | Ex. 3 (Hpβ-CD) | Ex. 4 (Hpβ-CD) | Ex. 5 (SBEβ-CD) | Ex. 6 (SBEβ-CD) |
|---|---|---|---|---|---|---|
| 1 | NPF: 100% | NPF: 100% | NPF: 96% | NPF: 97% | NPF: 96% | NPF: 97% |
| 3 | NPF: 98% | NPF: 99% | NPF: 91% | NPF: 92% | precipitate | NPF: 90% |
| 6 | NPF: 97% | NPF: 98% | NPF: 80%– | NPF: 84% | | precipitate |
| 9 | NPF: 96% | NPF: 97% | — | — | — | — |
| 12 | NPF: 95% | NPF: 96% | — | — | — | — |

-continued

| Months 25° C. | Ex. 1 (Metβ-CD) | Ex. 2 (Metβ-CD) | Ex. 3 (Hpβ-CD) | Ex. 4 (Hpβ-CD) | Ex. 5 (SBEβ-CD) | Ex. 6 (SBEβ-CD) |
|---|---|---|---|---|---|---|
| 18 | NPF: 93% | NPF: 95% | — | — | — | — |
| 24 | NPF: 92% | NPF: 94% | — | — | — | — |

As the results of the performed assays show, the formulations containing NPF complexed by Metβ-CDs have a considerable further stabilization when formulated in the presence of hydrophilic polymers, in particular polyvinyl pyrrolidone (PVP) and polyvinyl alcohol (PVA). These polymers allow increasing the stability of NPF up to 98% after 24 months of storage at 25° C., limiting degradation to a few by-products, each of these not exceeding 1% with respect to the nominal titer of NPF. Such advantage is not observed when NPF is formulated with cyclodextrins other than Metβ-CD.

Example 7

Stability

Tables 5-10 below show the results of the stability studies conducted on formulations 1-6 described in the present patent application.

TABLE 5

Stability study at 25° C. of formulation 1
Month (T)

| Time 25° C. | T3 | T6 | T9 | T12 | T18 | T24 |
|---|---|---|---|---|---|---|
| % NPF | 100 | 99 | 98 | 98 | 97 | 96 |
| pH | 7.5 | 7.5 | 7.5 | 7.5 | 7.4 | 7.4 |
| Appearance | Conf | Conf | Conf | Conf | Conf | Conf |

TABLE 5

Stability study at 25° C. of formulation 2
Month (T)

| Time 25° C. | T3 | T6 | T9 | T12 | T18 | T24 |
|---|---|---|---|---|---|---|
| % NPF | 100 | 99 | 98 | 97 | 96 | 95 |
| pH | 7.5 | 7.5 | 7.4 | 7.4 | 7.3 | 7.3 |
| Appearance | Conf | Conf | Conf | Conf | Conf | Conf |

TABLE 7

Stability study at 25° C. of formulation 3
Month (T)

| Time 25° C. | T3 | T6 | T9 | T12 | T18 | T24 |
|---|---|---|---|---|---|---|
| % NPF | 100 | 99 | 98 | 98 | 97 | 96 |
| pH | 7.6 | 7.6 | 7.6 | 7.6 | 7.5 | 7.5 |
| Appearance | Conf | Conf | Conf | Conf | Conf | Conf |

TABLE 8

Stability study at 25° C. of formulation 4
Month (T)

| Time 25° C. | T3 | T6 | T9 | T12 | T18 | T24 |
|---|---|---|---|---|---|---|
| % NPF | 100 | 100 | 100 | 99 | 98 | 98 |
| pH | 7.8 | 7.8 | 7.8 | 7.8 | 7.7 | 7.7 |
| Appearance | Conf | Conf | Conf | Conf | Conf | Conf |

TABLE 9

Stability study at 25° C. of formulation 5
Month (T)

| Time 25° C. | T3 | T6 | T9 | T12 | T18 | T24 |
|---|---|---|---|---|---|---|
| % NPF | 100 | 100 | 99 | 99 | 98 | 98 |
| pH | 7.8 | 7.8 | 7.7 | 7.7 | 7.7 | 7.7 |
| Appearance | Conf | Conf | Conf | Conf | Conf | Conf |

TABLE 10

Stability study at 25° C. of formulation 6
Month (T)

| Time 25° C. | T3 | T6 | T9 | T12 | T18 | T24 |
|---|---|---|---|---|---|---|
| % NPF | 100 | 100 | 100 | 99 | 98 | 98 |
| pH | 7.8 | 7.8 | 7.8 | 7.7 | 7.7 | 7.7 |
| Appearance | Conf | Conf | Conf | Conf | Conf | Conf |

Example 8

Stability

Tables 11-15 show the stability studies at 25° C. of formulations 9-13, for which the presence of a cortisone or omega-3 is contemplated.

TABLE 11

Stability study at 25° C. of formulation 9.
Month (T)

| Time 25° C. | T3 | T6 | T9 | T12 | T18 | T24 |
|---|---|---|---|---|---|---|
| % NPF | 100 | 100 | 99 | 98 | 97 | 97 |
| % DEX-P | 100 | 99 | 98 | 97 | 95 | 93 |
| pH | 7.6 | 7.6 | 7.6 | 7.6 | 7.6 | 7.5 |
| Appearance | Conf | Conf | Conf | Conf | Conf | Conf |

TABLE 12

Stability study at 25° C. of formulation 10
Month (T)

| Time 25° C. | T3 | T6 | T9 | T12 | T18 | T24 |
|---|---|---|---|---|---|---|
| % NPF | 100 | 99 | 98 | 97 | 97 | 97 |
| % HYD-P | 100 | 99 | 98 | 97 | 96 | 94 |

TABLE 12-continued

Stability study at 25° C. of formulation 10 Month (T)

| Time 25° C. | T3 | T6 | T9 | T12 | T18 | T24 |
|---|---|---|---|---|---|---|
| pH | 7.6 | 7.6 | 7.5 | 7.4 | 7.4 | 7.3 |
| Appearance | Conf | Conf | Conf | Conf | Conf | Conf |

TABLE 13

Stability study at 25° C. of formulation 11 Month (T)

| Time 25° C. | T3 | T6 | T9 | T12 | T18 | T24 |
|---|---|---|---|---|---|---|
| % NPF | 100 | 100 | 100 | 99 | 98 | 97 |
| % DEX-OH | 100 | 99 | 99 | 99 | 99 | 98 |
| pH | 7.8 | 7.8 | 7.8 | 7.8 | 7.7 | 7.7 |
| Appearance | Conf | Conf | Conf | Conf | Conf | Conf |

TABLE 14

Stability study at 25° C. of formulation 12 Month (T)

| Time 25° C. | T3 | T6 | T9 | T12 | T18 | T24 |
|---|---|---|---|---|---|---|
| % NPF | 100 | 100 | 99 | 99 | 98 | 98 |
| % DHA-EE | 100 | 99 | 98 | 96 | 94 | 92 |
| pH | 7.8 | 7.8 | 7.8 | 7.8 | 7.7 | 7.7 |
| Appearance | Conf | Conf | Conf | Conf | Conf | Conf |

TABLE 15

Stability study at 25° C. of formulation 13. Month (T)

| Time 25° C. | T3 | T6 | T9 | T12 | T18 | T24 |
|---|---|---|---|---|---|---|
| % NPF | 100 | 100 | 99 | 98 | 96 | 95 |
| % EPA-AA | 100 | 99 | 97 | 96 | 93 | 92 |
| pH | 7.6 | 7.6 | 7.6 | 7.5 | 7.4 | 7.4 |
| Appearance | Conf | Conf | Conf | Conf | Conf | Conf |

In such formulations, the further active ingredients (DEX-P, HYD-P, DEX-OH and EPA and DHA) show a chemical stability which is greater than 90% after 24 months at 25° C., and, as can be surprisingly seen, their presence does not affect the stability of NPF.

From what has been described above, the advantages provided by the formulations of the invention will become apparent to the man skilled in the art.

Firstly, it is possible to prepare liquid ophthalmic formulations highly desired by patients and therefore showing high acceptability (compliance).

The formulations have furthermore shown high stability, from both a physical and a chemical point of view, contributing to a surprisingly long shelf life, up to 24 months.

The presence of further active ingredients within the formulations of the invention does not lead in any way to a decrease in their stability; therefore, the present invention allows preparing formulations containing more than one medicament.

What is claimed:

1. An ophthalmic pharmaceutical formulation comprising Nepafenac, methyl-β-cyclodextrin, polyvinyl pyrrolidone (PVP), polyvinyl alcohol (PVA), and hyaluronic acid, wherein the Nepafenac is present in an amount comprised between about 0.1% and about 0.5%, by weight of the total weight of the ophthalmic pharmaceutical formulation,
   wherein the methyl-β-cyclodextrin is present in an amount comprised between about 1% and about 5% by weight of the total weight of the ophthalmic pharmaceutical formulation,
   wherein the polyvinyl pyrrolidone (PVP) and polyvinyl alcohol (PVA) are each present in an amount comprised between about 0.5% and about 1.5% by weight of the total weight of the ophthalmic pharmaceutical formulation, and
   wherein the hyaluronic acid is present in an amount comprised between about 0.1% and about 0.15% by weight of the total weight of the ophthalmic pharmaceutical formulation.

2. The ophthalmic pharmaceutical formulation of claim 1, further comprising one or more additional active ingredients.

3. The ophthalmic pharmaceutical formulation of claim 2, wherein said active ingredients comprise: polyunsaturated fatty acids or derivatives thereof, cortisones.

4. The ophthalmic pharmaceutical formulation of claim 1, having a pH comprised between about 7.1 and about 7.9.

5. The ophthalmic pharmaceutical formulation of claim 1, further comprising at least one: preservatives, a buffer system, osmotizing agents.

6. A process for preparing the ophthalmic pharmaceutical formulation of claim 1, the process comprising the steps of solubilizing Nepafenac in a solution comprising methyl-β-cyclodextrin and optionally a hydrophilic polymer selected from the group consisting of polyvinyl pyrrolidone (PVP), polyvinyl alcohol (PVA) and hyaluronic acid, said solution having a pH comprised between about 7.1 and about 7.9 adding osmotizing agents, any other hydrophilic polymers and, subsequently, adjusting the pH to a desired value.

7. A method for stabilizing an ophthalmic pharmaceutical formulation of claim 1 comprising Nepafenac, said method comprising adding methyl-β-cyclodextrin to said ophthalmic pharmaceutical formulation.

8. A method for treating post-surgical inflammatory and/or painful states, retinal neurodegenerative diseases, and for preventing cystoid macular edema in a subject in need thereof, said method comprising administering to said subject the ophthalmic pharmaceutical formulation of claim 1.

* * * * *